United States Patent [19]
Dussaud et al.

[11] Patent Number: 4,801,345
[45] Date of Patent: Jan. 31, 1989

[54] PROCESS FOR MANUFACTURING DISPOSABLE DIAPERS AND DIAPER BRIEFS, AND DISPOSABLE DIAPERS AND DIAPER BRIEFS OBTAINED BY APPLICATION OF THIS PROCESS

[75] Inventors: Jacques Dussaud, Lille; Raphael DE Jonckheere, Bondues, both of France

[73] Assignee: Boussac Saint Freres B.S.F., Lille, France

[21] Appl. No.: 605,970

[22] Filed: May 1, 1984

Related U.S. Application Data

[63] Continuation of Ser. No. 301,262, Sep. 11, 1981, abandoned.

[30] Foreign Application Priority Data

Sep. 15, 1980 [FR] France ................ 80 19862

[51] Int. Cl.$^4$ .................. B29C 65/48; B32B 31/08
[52] U.S. Cl. ..................... 156/164; 156/229
[58] Field of Search ........... 156/164, 229, 494, 495, 156/498, 256, 269, 201

[56] References Cited

U.S. PATENT DOCUMENTS

| | | | |
|---|---|---|---|
| 3,150,023 | 9/1964 | Penman | 156/498 |
| 3,828,367 | 8/1974 | Bourgeois | 156/164 |
| 3,950,207 | 4/1976 | Amat | 156/498 |
| 4,081,301 | 3/1978 | Buell | 156/164 |
| 4,293,367 | 10/1981 | Klasek | 156/164 |
| 4,352,355 | 10/1982 | Mesek et al. | 604/385 |
| 4,405,397 | 9/1983 | Teed | 156/164 |

Primary Examiner—Merrell C. Cashion, Jr.
Attorney, Agent, or Firm—Millen & White

[57] ABSTRACT

Adhesive is intermittently coated onto an elastic strip 4 which then passes over a grooved pulley 9 mounted on a slide or carriage 10 able to move intermittently on a slideway 11. A continuous flexible sheet consisting of a moisture-impermeable heat-sealable material is unreeled over the periphery of a rotary drum 3. The point of contact between the elastic strip 4, and the travelling impermeable sheet 2 is moved periodically in a direction transverse to the direction of travel of the sheet 2. This results in laying, along a curved path 4a of, a stretched elastic adhered to sheet 2. It is thus possible to make diaper units comprising crotch elastics edging the curvilinear profile of the leg openings or cut-outs.

10 Claims, 4 Drawing Sheets

PROCESS FOR MANUFACTURING DISPOSABLE DIAPERS AND DIAPER BRIEFS, AND DISPOSABLE DIAPERS AND DIAPER BRIEFS OBTAINED BY APPLICATION OF THIS PROCESS

This is a continuation of application Ser. No. 301,262 filed Sept. 11, 1981, now abandoned.

BACKGROUND OF THE INVENTION

The present invention relates to a process for manufacturing disposable diapers and briefs having cut-outs for the leg openings which are curvilinear in shape and are provided over at least a part of their inner periphery with elastic elements improving leak-tightness around the leg openings.

Another object of the invention is also to provide the disposable diapers and briefs obtained by application of the process of the invention. These diapers or diaper briefs can be discarded after use and can be used for infants or for incontinent adults. They consist of an impermeable outer backing sheet, an absorbent pad forming an integral part of the assembly and preferably of a permeable facing web acting as the inner diaper liner.

In order to improve the seal around the leg openings of disposable diapers of this type it has already been suggested that rectilinear elastic strips be adhered in the stretched state onto an impermeable sheet designed to form the outer envelope of the diaper unit.

As an example of products of this type, mention may be made of the disposable diapers described in U.S. Pat. Nos. 3,860,003 and 4,050,462. The elastic elements placed near to the margin of the leg openings in such diapers in order to improve the leaktightness at this spot must not, however, grip too tightly or lead to folds being formed in the material, and notably in the material forming the absorbent pad, in order to respect the user's anatomy whether this is an adult or an infant.

In order to improve the profile of diapers fitted with such crotch elastics, a special absorbent pad structure has already been designed, as described in French patent application No. 2,438,434.

The operation of making curvilinear shaped openings or crotch cut-outs has so far meant that it was not possible to manufacture, continuously on an industrial scale and at a high rate, this type of diaper having elastics round the edge, owing to the curved shape of the periphery.

Disposable diapers of this type having an elastic tape on the edge of the curvilinear leg opening as described in French Pat. No. 2,063,794 can only be made by methods which are not very suitable for high-output manufacture, notably by sewing elastic tapes or threads.

SUMMARY OF THE INVENTION

The object of the present invention is to provide a manufacturing process which makes it possible to make simply, and at high speed, disposable diaper units of this type comprising elastic elements edging the curvilinear shape of the leg openings; thus improving the seal at this spot at the same time as retaining leg openings which are shaped to fit the user's anatomy.

The continuous manufacturing process according to the invention makes it possible to manufacture disposable diapers comprising an absorbent pad placed between an outer moisture-impermeable envelope and a permeable inner facing; the assembly comprises curvilinear shaped cut-outs to let the legs through, these cut-outs being provided with elastic elements round the inside edge.

According to the invention, a hot melt adhesive material is laid at high temperature on the face of an elastic strip travelling in the stretched state and intended to come into contact with a continuous flexible backing sheet consisting of a moisture-impermeable heat-sealable material. The point of contact between the adhesive-coated elastic strip and the travelling impermeable sheet is then moved periodically in a transverse direction with respect to the direction of the travel of the said impermeable backing sheet. In this way a crotch elastic having a curved shape is obtained, adhered in the stretched state along at least one curved portion of each leg opening cut-out. The impermeable sheet is preferably passed over the perimeter of a rotary drum kept at a relatively low temperature compared with the temperature of the molten adhesive. In this way the adhesive material deposited hot on the elastic strip before making contact with the impermeable sheet, is suddenly cooled as soon as it contacts the said impermeable sheet, which leads to immediate adhesion allowing a curvilinear elastic in the stretched state to be produced.

The temperature of the rotary drum can easily be chosen by the technician taking into consideration the parameters of the weight of the said drum or roll, the weight of adhesive per unit length of elastic strip, the temperature of the adhesive immediately before contact, the type of edhesive and the curvature required for the crotch elastic.

In this respect the temperature difference between the adhesive laid down and the outer surface of the rotary drum should be sufficient to lead to an immediate adhesion effect capable of withstanding the transverse forces to which the strip is subjected owing to the travel of the contact point. In practice it is observed that a temperature difference of at least 20° C. is necessary and preferably from 70° C. to 130° C.

The point of contact between the elastic strip and the flexible impermeable sheet is preferably held fixed intermittently so as to define unglued rectilinear portions of the elastic strip separating adhered curvilinear portions.

The initial contact point between the elastic strip and the flexible impermeable sheet can be moved in the transverse direction by any suitable means. In a preferred embodiment, the stretched elastic strip is made to pass over a guide means like a slideway, possible curved, or a grooved pulley mounted immediately adjacent to the periphery of the rotary drum, on a slide or carriage capable of moving parallel to the drum axis with an alternating translational movement. The guide means may comprise means for holding the strip such as flanges or suction orifices to prevent the elastic strip from escaping from the guide means when it is moving. This movement may be driven, for example, by a cam system and indexed to the drum rotation so that the curvilinear portions of the elastic strips are provided at the right positions on the impermeable sheet.

The process of the invention can be applied to making diapers obtained by transversally cutting the continuous impermeable sheet. In this case the oblong-shaped absorbent pads are placed along the longitudinal axis of the impermeable sheet and the cut-outs are made on the longitudinal edges of the composite band formed by the impermeable backing sheet, the absorbent pad and the permeable inner facing.

The process of the invention can also be applied to making diaper briefs comprising a tie or band, preferably elastic, placed at the waist. In this case the oblong-shaped absorbent pads are laid perpendicularly to the longitudinal axis of the impermeable sheet and the leg opening cut-outs are made in the form of openings aligned along the longitudinal axis and symmetrically with respect to the transverse direction. The diaper briefs are then produced by subsequent folding along the longitudinal axis of the composite band followed by a parting accompanied by a simultaneous weld along the transverse axis of symmetry of the openings.

Another object of this invention is the disposable diaper obtained by the process of the invention.

Such a disposable diaper consists of an absorbent pad placed between an outer moisture-impermeable envelope and an inner permeable facing; the assembly comprises curvilinear shaped cut-outs to allow for the legs to pass through, provided round their inner edge with elastic elements. According to the invention, the diaper unit manufactured according to the process of the invention comprises curvilinear crotch elastics adhered along at least one curved portion of each leg opening cut-out.

BRIEF DESCRIPTION OF THE DRAWINGS

This invention will be better understood on study of the description of several embodiments, taken as examples, which are in no way limiting, and illustrated by the appended drawings in which.

DETAILED DISCUSSION OF THE INVENTION

Figure 1:
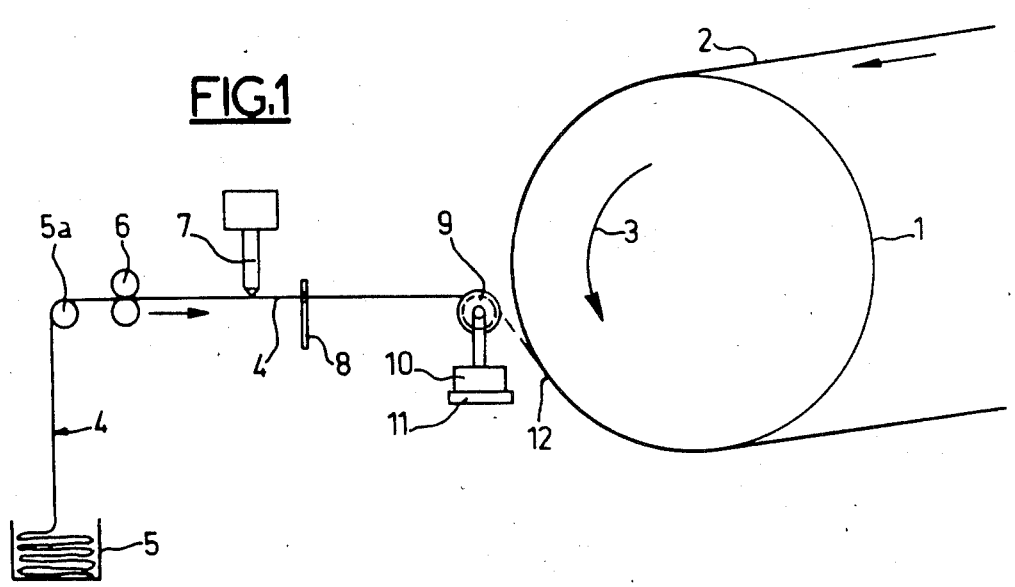
FIG. 1 is a schematic side view of the main components of an installation set up for application of the process of the invention.
Figure 2:
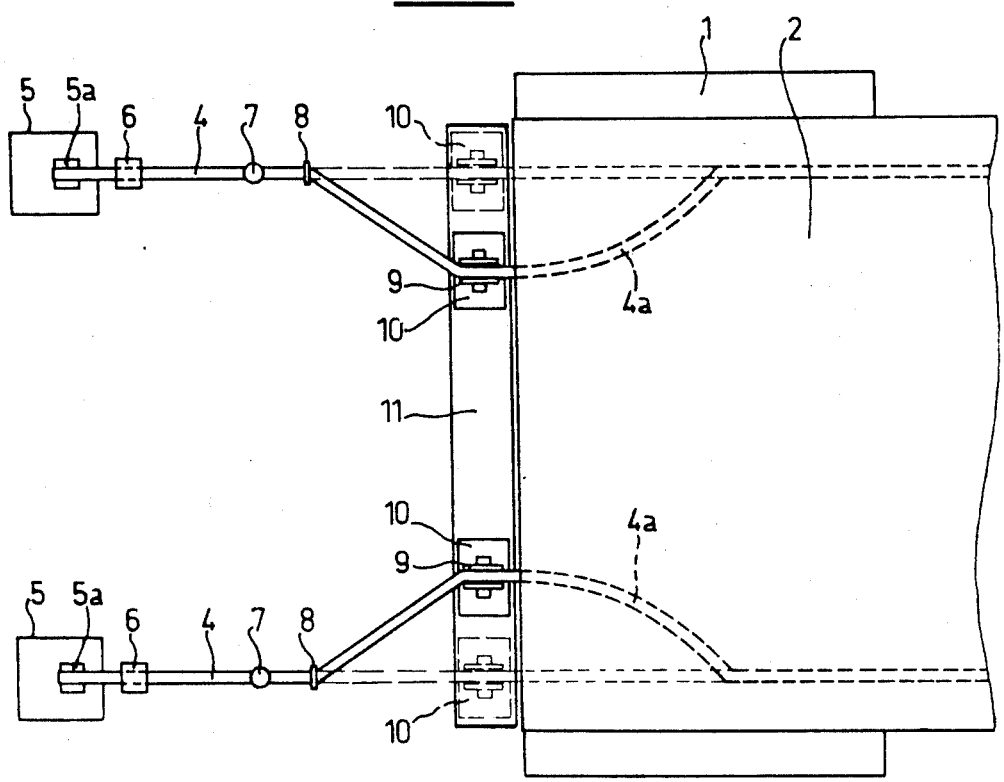
FIG. 2 is a top view of the components of FIG. 1.

As shown schematically in FIGS. 1 and 2, the installation permitting application of the process of the invention comprises a rotary drum 1 around which is wound a continuous flexible sheet 2 of a moisture-impermeable heat-sealable material like polyethylene. The drum 1 is driven in rotation in the direction of the arrow 3 so that the sheet 2 fits round about half the circumference of the rotary drum 1. The drum is held at a relatively low temperature of around 20° C. This temperature may be maintained by forced artificial cooling inside the drum or simply by using a drum with sufficient mass.

Two narrow elastic strips 4 made, for example, of latex are stored in containers 5. After being withdrawn from the containers 5 the elastic strips 4 pass over a guide roller 5a and then between two tension rollers 6 driven in rotation in such a way that the linear travel speed of the elastic strip 4 leaving the tension rollers 6 is less than the peripheral speed of the impermeable sheet 2 over the rotary drum 1.

By suitably adjusting the speed difference the required elongation of the elastic strip 4 is obtained.

An adhesive material at high temperature, for example around 100° C. to 150° C., made liquid by melting (hot melt adhesive) is delivered intermittently by the nozzle 7 in the form of a fine line on the surface of the elastic strip 4 meant to come into contact with the impermeable sheet 2. A valve, not shown in the figure, enables the adhesive material feed to be suspended automatically for predetermined periods of time. The elastic strip 4, which may or may not be coated with a line of adhesive material, then passes inside a fixed guide element 8 followed by a grooved pulley 9, mounted on a mobile slide 10 which can slide in a slideway 11 actuated by control components not shown in the figures. These control components may, for example, consist of cams or similar elements. After passing over the grooved pulley 9, the elastic strip 4 comes into contact with the impermeable sheet 2 at the edge of the rotary drum 3, the contact point being marked 12 in the figures. The grooved pulley 9 is placed right next to the periphery of the rotary drum 1. In the example illustrated the contact point 12 is slightly downstream of the mid-point of the circumferential path of the impermeable sheet 2 over the rotary drum. The contact point could also be placed further upstream on the sheet 2 path so as to increase the period of cooling of the adhesive in contact with the drum 1. The elastic strip 4 travels from the grooved pulley 9 up to contact with the impermeable sheet 2 located on the periphery of the rotary drum 1 and in a direction tangential to the profile of the rotary drum 1.

Under these conditions, owing to the temperature difference between the drum and the adhesive, the molten adhesive material lying on the surface of the elastic strip 4 sets immediately after contact leading to immediate adhesion, so that the movement of the slides 10 and the contact points 12 in a transverse direction enables the elastic strip to be adhered following a curvilinear profile 4a, as can be seen in FIG. 2. The temperature difference, because of the respective masses of the adhesive applied in a very thin line and the rotary drum, is sufficient for the adhesive to set on contact and withstand the transverse force due to laying the strip along a curved path.

In FIG. 2 we have also shown by a broken line the positon taken up by the slides 10 for laying the rectilinear portions of the elastic strips. It will be noticed in FIG. 2 that the angle formed by the elastic strip on leaving the guide element 8 has been exaggerated to make the drawing clearer. In practice it is arranged that this maximum angle does not create a risk leading to the strip 4 slipping out of the grooved pulleys 9. In another version the rotating pulleys may be replaced by slideways or other means of guiding and holding the travelling elastic strip.

Figure 3:
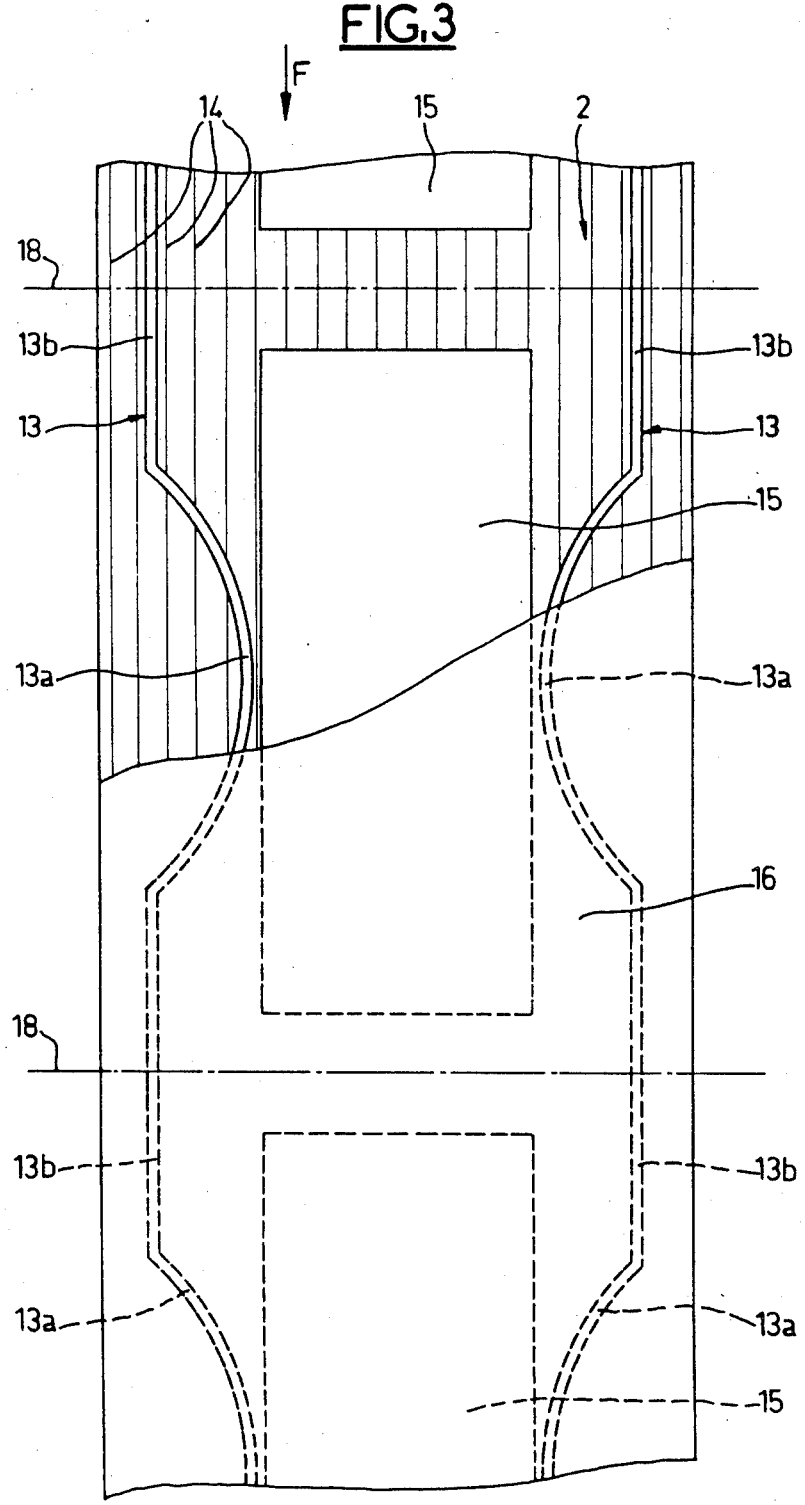
FIG. 3 is a partly broken-away view of a composite band illustrating the various stages in the manufacture of a diaper according to the invention.

In the embodiment illustrated in FIG. 3 the impermeable sheet 2, which travels in the direction of the arrow F parallel to the longitudinal axis X—X, receives along its two longitudinal margins two continuous elastics 13. The concave curvilinear portions 13a are coated with adhesive in the stretched state according to the process which has been described in reference to FIGS. 1 and 2, while the rectilinear portions 13b which connect them together are not coated with adhesive. Continuous adhesive lines 14 are laid on the surface of the impermeable sheet in another stage of the process to enable rectangular oblong absorbent pads 15 and a moisture-permeable facing web 16 to be adhered to it.

Figure 4:
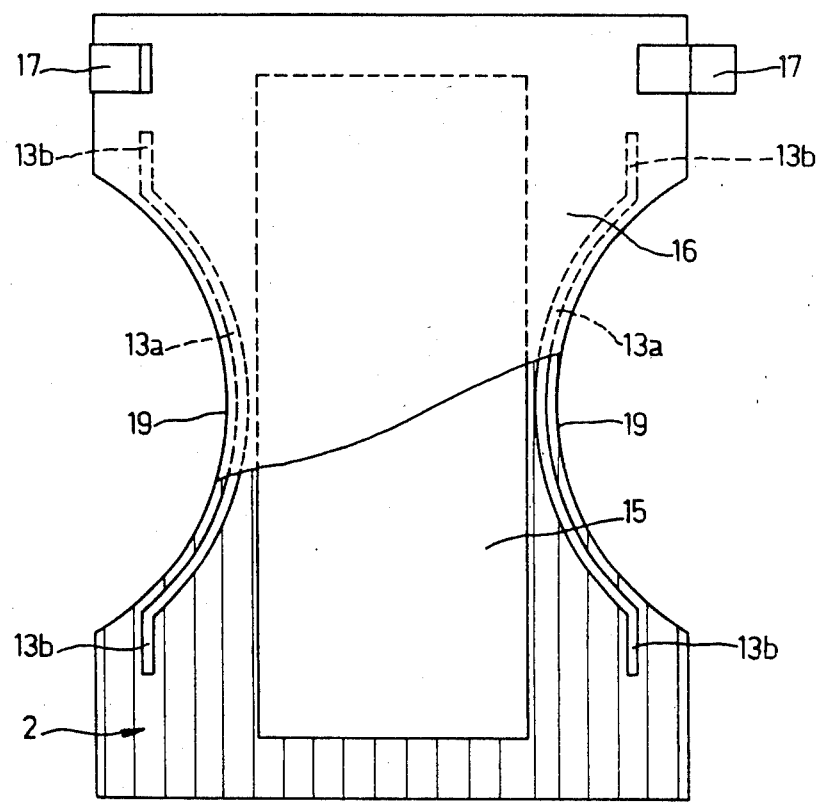
FIG. 4 is an elevation view of a disposable diaper made from the composite band of FIG. 3.

After installing adhesive tape devices 17 on the longitudinal margins of the sheet 2, and after cutting the curved cut-outs and simultaneous welding carried out on the longitudinal margins of the composite band formed by sheet 2, the absorbent pads 15 and the permeable facing 16, the final manufacturing stage is carried out, which consists of cutting the composite band transversally along lines 18 so as to form diapers like the one illustrated in FIG. 4. In the cutting operation the rectilinear portions 13b of the crotch elastics 13 are parted; the remaining portions return to their original length and remain captive between the impermeable backing sheet 2 and the permeable facing 16.

As can be seen in FIG. 4 a diaper is finally obtained in which the leg openings 19 have a concave curved profile which perfectly fits the user's anatomy, the profile 19 being edged on the inside with a curvilinear elastic 13a laid in the stretched state and providing an appropriate seal at this spot.

Although the absorbent pad has been shown in FIG. 4 as having a rectangular shape it will be understood that it could also have an hour-glass shape following the leg opening profile 19.

Figure 6:
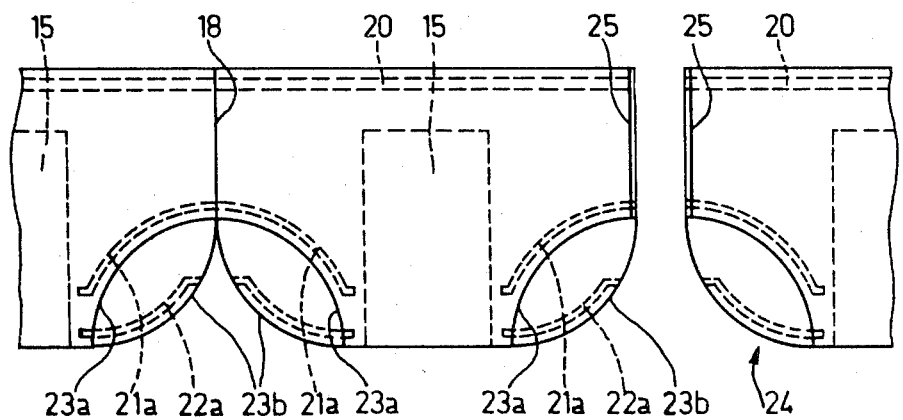
FIG. 6 shows the final stage of manufacture in the variation shown in FIG. 5.
Figure 5:
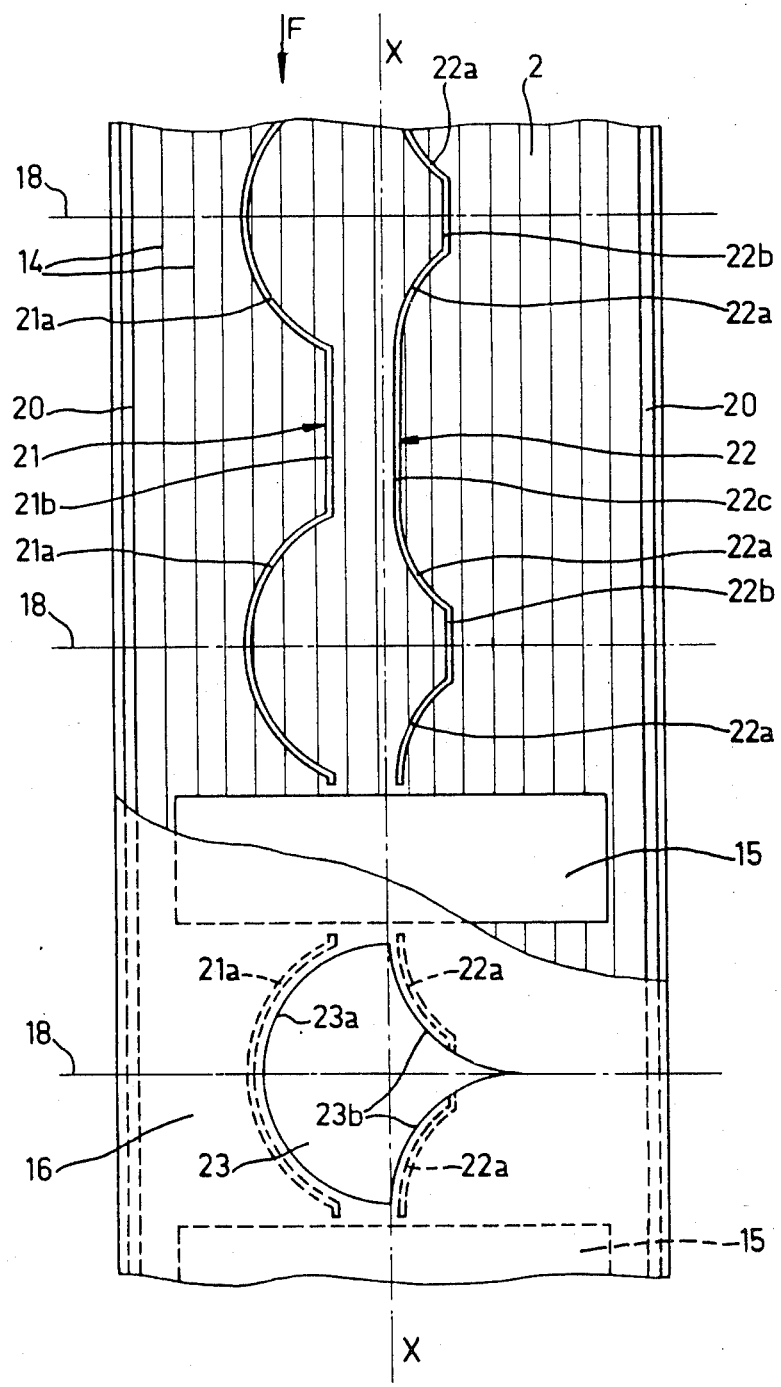
FIG. 5 is a composite band illustrating manufacture in accordance with a variation of the invention.

In the embodiment illustrated in FIGS. 5 or 6 in which identical elements have the same reference numbers, the impermeable sheet 2, travelling as before in the direction of the arrow F parallel to the longitudinal axis X—X, first of all receives along its two longitudinal margins a rectilinear continuous elastic 20 coated with adhesive over its whole surface in the stretched state and designed to form an elastic tightening the waist of the diaper over all or part of the waist length. The crotch elastics are formed by two elastic strips 21 and 22 coated intermittently with adhesive respectively on either side of the longitudinal axis X—X. The elastic strip 21 comprises curvilinear portions 21a round the future leg openings and shaped like semicircles which are symmetrical about the transverse lines 18 and cut these latter lines at right angles. These curvilinear portions 21a coated with adhesive throughout their length, and obtained by the process illustrated in FIGS. 1 and 2, are connected together by unglued rectilinear portions 21b parallel to the longitudinal axis X—X.

The elastics 22 comprise two curvilinear portions 22a coated with adhesive throughout their length and positioned on either side of the transverse line 18 and symmetrically with respect to this line, in the form of an arc of circle which is convex with respect to the future leg opening. The adhesive-coated portions 22a are connected by an unglued rectilinear portion 22b intersecting the transverse line 18 and parallel with the axis X—X and a second unglued rectilinear portion 22c parallel with the axis X—X and close to it.

During a subsequent operation the unglued rectilinear portions 21b and 22c are parted and removed, or simply released, so as to allow the laying of the rectangular oblong absorbent pads 15, which are this time laid transversally, i.e. perpendicular to the longitudinal axis X—X, between two transverse lines 18. The absorbent pads 15 are adhered as previously by means of the existence of the adhesive lines 14.

After the permeable facing 16 has been laid and adhered, the leg openings 23 are simultaneously cut out and welded round their edges; the profile of these leg openings 23 comprises a first arc of circle 23a which is concave and parallel to the arc of the portion 21a of elastic 21 and two convex arc of circle portions 23b which are parallel respectively to the arcs of circle 22a of elastic 22. The point formed by the two arcs of circle 23b which join roughly tangentially on the transverse line 18 means that the rectilinear unglued portion 22b of elastic 22 is cut at the same time.

Manufacture is completed by folding around the longitudinal axis X—X so as to obtain the continuous product shown on the left of FIG. 6.

A cutting operation accompanied by simultaneous welding enables diaper briefs to be made like the diaper brief 24 which has a weld along its side edge. The diaper thus obtained is therefore like a pair of briefs and is put on in the same way, the waist elastic 20 being made continuous by the two side welds 25.

In all cases the process of the invention allowing curvilinear shaped elastic elements to be laid in the stretched state therefore enables crotch elastics to be made following the curvilinear leg opening profile which is most suited to the user's anatomy.

I claim:

1. A method of continuously attaching an elongated narrow elastic element to a moving flexible sheet material to be employed as an outer moisture impermeable envelope for receiving an absorbent pad of a disposable diaper, said elastic element fitting in a stretched condition substantially along a curvilinear-shaped-cut-out of said envelope to allow a leg therethrough when said envelope is constructed as a diaper, said method comprising the steps of:

(a) passing an elongated narrow elastic element, along a longitudinal path of travel, in a stretched condition;

(b) intermittently depositing liquid adhesive material at high temperature on said elastic element during said passing step (a);

(c) passing said elastic element, with adhesive material thereon, over a fixed guide means;

(d) passing said elastic element with adhesive material over a carriage means, arranged down-stream of the fixed guide means in the direction of travel, and being movable intermittently in a transverse direction;

(e) feeding a flexible sheet around the peripheral surface of a rotary drum such that the sheet remains in contact with said drum for about one-half the rotation of said drum, said drum having a smooth outer surface which is maintained at a substantially constant temperature, said temperature being less than the temperature of said liquid adhesive, the difference between the temperature of the adhesive at the time of contact with said flexible sheet and the temperature of said peripheral surface of the drum being at least 20° C.; and (f) positions said movable carriage immediately next to the periphery of said rotary drum at a location such that said carriage means and said drum are not in contact with each other and such that the adhesive coated elastic element contacts said flexible sheet supported by said drum, and said sheet together with said elastic element remain in contact with said drum for at least a portion of the rotation of said rotary drum before leaving it, moving said carriage means intermittently in a direction transverse to the direction of rotation of said drum and said temperature difference being sufficient to lead to an immediate adhesion effect capable of withstanding the transverse forces to which said elastic element is subjected owing to the movement of said carriage means whereby said elastic element is laid-down on said drum in an oscillating path, and whereby said elastic element is intermittently attached in a stretched condition along a curved-shaped line by laying said elastic element on said flexible sheet due to the temperature difference between the drum and the adhesive material;

and with the provision that steps (e) and (f) are conducted on a single drum.

2. A method as in claim 1, wherein the temperature difference in step (e) is 70°–130° C.

3. A method as in claim 1, wherein the carriage means is held intermittently fixed so as to define unglued rectilinear portions of the elastic strips separating the adhered curved-shaped line portions.

4. A method as in claim 1, wherein the point at which the adhesive coated elastic element contacts the flexible sheet supported by said drum is located slightly upstream along the path of travel of the midpoint of the peripheral path of the impermeable sheet over the drum.

5. A method as in claim 1, wherein the stretched elastic strip is passed over a guide means mounted immediately next to the periphery of the rotary drum on the carriage means which is capable of moving parallel to the axis of the drum with a reciprocating translational movement.

6. A method of manufacturing a disposable diaper having elastic portions and made up of an outer moisture impermeable envelope receiving an absorbent pad thereon, an inner permeable facing and elastic elements fitting in a stretched condition substantially along a curvilinear-shaped-cut-out of said envelope in a central crotch fitting area, and comprising the steps of:
(a) passing an elongated narrow element, along a longitudinal path of travel, in a stretched condition;
(b) intermittently depositing liquid adhesive material at high temperature on said elastic element during said passing step (a);
(c) passing said elastic element, with adhesive material thereon, over a fixed guide means;
(d) passing said elastic element with adhesive material over a carriage means, arranged down-stream of the fixed guide means in the direction of travel, and being movable intermittently in a transverse direction;
(e) feeding a flexible sheet around the peripheral surface of a rotary drum such that said sheet remains in contact with said drum for about one-half the rotation of said drum, said drum having a smooth outer surface which is maintained at a substantially constant temperature, said temperature being less than the temperature of said liquid adhesive, the difference between the temperature of the adhesive at the time of contact with said flexible sheet and the temperature of said peripheral surface of the drum being at least 20° C.; and
(f) positioning said movable carriage immediately next to the periphery of said rotary drum at a location such that said carriage means and said drum are not in contact with each other and such that the adhesive coated elastic element contacts said flexible sheet supported by said drum and said sheet together with said elastic element remain in contact with said drum for at least a portion of the rotation of said rotary drum before leaving it, moving said carriage means intermittently in a direction transverse to the direction of rotation of the drum, said temperature difference being sufficient to lead to an immediate adhesive effect capable of withstanding the transverse forces to which said elastic element is subjected owing to the movement of said carriage means whereby said elastic element is laid-down on said drum in an oscillating path, and whereby said elastic element is intermittently attached in a stretched condition along a curved-shaped line to said flexible sheet, with said attaching being effected only due to the temperature difference between the drum and the adhesive material;

and with the provision that steps (e) and (f) are conducted on a single drum.

7. A method as in claim 6, wherein the absorbent pads are placed along the longitudinal axis of the impermeable sheet, the cut-outs are made in the longitudinal margins of the composite band formed by the impermeable sheet, the absorbent pads and the inner facing; and the diapers are finally obtained by transverse cutting.

8. A method as in claim 6, wherein the absorbent pads are placed perpendicular to the longitudinal axis of the impermeable sheet, cut-outs are made in the form of openings along the longitudinal axis symmetrical with respect to a transverse direction, and the diaper units are finally obtained by folding along the longitudinal axis followed by an operation of cutting and welding along the transverse axis of symmetry of the openings.

9. A method as in claim 8, further comprising adhering a rectilinear continuous elastic in the stretched state throughout the length of each longitudinal margin of the impermeable sheet to define an elastic grip at the waist of the diaper brief after assembly thereof.

10. A method of continuously attaching an elongated narrow elastic element to a moving flexible sheet material to be employed as an outer moisture impermeable envelope for receiving an absorbent pad of a disposable diaper, said elastic element fitting in a stretched condition substantially along a curvilinear-shaped-cut-out of said envelope to allow a leg therethrough when said envelope is constructed as a diaper, said method comprising the steps of:
(a) passing an elongated narrow elastic element, along a longitudinal path of travel, in a stretched condition;
(b) intermittently depositing liquid adhesive material at high temperature on said elastic element;
(c) passing said elastic element over a fixed guide means;
(d) passing said elastic element over a carriage means, arranged down-stream of the fixed guide means in the diection of travel, and being movable intermittently in a transverse direction.
(e) feeding a flexible sheet around the peripheral surface of a rotary drum such that the sheet remains in contact with said drum for about one-half the rotation of said drum, said drum having a smooth outer surface which is maintained at a substantially constant temperature, said temperature being less than the temperature of said liquid adhesive, the difference between the temperature of the adhesive at the time of contact with said flexible sheet and the temperature of said peripheral surface of the drum being at least 20° C.; and
(f) positioning said movable carriage immediately next to the periphery of said rotary drum at a location such that said carriage means and said drum are not in contact with each other and such that the adhesive coated elastic element contacts said flexible sheet supported by said drum, and said sheet together with said elastic element remain in contact with said drum for at least a portion of the rotation of said rotary drum before leaving it, moving said carriage means intermittently in a direction transverse to the direction of rotation of said drum, said temperature difference being sufficient to lead to an immediate adhesion effect capable of withstanding the transverse forces to which said elastic element is subjected owing to the movement of said carriage means whereby said elastic element is laid-down on said drum in an oscillating path, and whereby said elastic element is intermittently attached in a stretched condition along a curved-shaped line by laying said elastic element on said flexible sheet due to the temperature difference between the drum and the adhesive material;

and with the provision that steps (e) and (f) are conducted on a single drum and said temperature difference is sufficient to lead to an immediate adhesion effect capable of withstanding the transverse forces to which said elastic element is subjected owing to the movement of said carriage means.

* * * * *